(12) United States Patent
Kogane

(10) Patent No.: US 11,064,126 B2
(45) Date of Patent: Jul. 13, 2021

(54) MULTI-POSITIONING CAMERA SYSTEM AND CAMERA SYSTEM

(71) Applicant: PANASONIC I-PRO SENSING SOLUTIONS CO., LTD., Fukuoka (JP)

(72) Inventor: Haruo Kogane, Fukuoka (JP)

(73) Assignee: PANASONIC I-PRO SENSING SOLUTIONS CO., LTD., Fukuoka (JP)

( * ) Notice: Subject to any disclaimer, the term of this patent is extended or adjusted under 35 U.S.C. 154(b) by 0 days.

(21) Appl. No.: 16/884,644

(22) Filed: May 27, 2020

(65) Prior Publication Data

US 2020/0382714 A1 Dec. 3, 2020

(30) Foreign Application Priority Data

May 30, 2019 (JP) .............................. JP2019-101816

(51) Int. Cl.
*A61B 1/04* (2006.01)
*H04N 5/232* (2006.01)
(Continued)

(52) U.S. Cl.
CPC ....... *H04N 5/23299* (2018.08); *H04N 5/2252* (2013.01); *H04N 5/2256* (2013.01);
(Continued)

(58) Field of Classification Search
CPC ..... A61B 1/042; A61B 1/127; A61B 1/00193; A61B 1/04; A61B 1/00009;
(Continued)

(56) References Cited

U.S. PATENT DOCUMENTS

| | | | |
|---|---|---|---|
| 2003/0208207 A1* | 11/2003 | Layer ..................... | A61B 90/11 606/130 |
| 2009/0118575 A1* | 5/2009 | Ichikawa ............. | A61B 1/0051 600/103 |
| 2013/0310646 A1* | 11/2013 | Dejima ................ | A61B 1/0016 600/114 |

FOREIGN PATENT DOCUMENTS

JP      2005-031900 A      2/2005

OTHER PUBLICATIONS

U.S. Appl. No. 16/785,095 to Shigeki Ogata et al., filed Feb. 7, 2020.

* cited by examiner

*Primary Examiner* — Masum Billah
(74) *Attorney, Agent, or Firm* — Greenblum & Bernstein, P.L.C.

(57) ABSTRACT

A multi-positioning camera system includes an industrial endoscope having an imaging device provided in a tip portion of a flexible soft portion; a reel mechanism which pays out and takes up the soft portion by rotating, in a normal direction and a reverse direction, a reel drum; a support pipe which supports the soft portion inserted from a tip of the support pipe in a pay-out direction; a distributor which switches and places a tip portion of the soft portion paid out from a support pipe opening formed at an insertion tip of the support pipe at one of a plurality of different positions; and plural branch pipes which have reception holes formed corresponding to the plural different positions, and observation windows that communicate with the reception holes and are located at the plural different positions, and each of which receives the soft portion inserted through the reception hole.

6 Claims, 14 Drawing Sheets

(51) Int. Cl.
*H04N 5/225* (2006.01)
*H04N 5/247* (2006.01)
(52) U.S. Cl.
CPC ........... *H04N 5/2257* (2013.01); *H04N 5/247* (2013.01); *H04N 2005/2255* (2013.01)
(58) Field of Classification Search
CPC .... A61B 2034/2057; A61B 2090/3616; A61B 2090/3618; A61B 2090/371; A61B 34/20; A61B 90/20
USPC ......................................................... 348/68
See application file for complete search history.

MULTI-POSITIONING CAMERA SYSTEM AND CAMERA SYSTEM

CROSS-REFERENCE TO RELATED APPLICATIONS

This application is based on and claims priority under 35 USC 119 from Japanese Patent Applications No. 2019-101816 filed on May 30, 2019, the contents of which are incorporated herein by reference.

TECHNICAL FIELD

The present disclosure relates to a multi-positioning camera system and a camera system.

BACKGROUND ART

Patent document 1 discloses a conveyance monitoring system that is employed in an automatic conveying system and makes it possible to shorten the recovery time from occurrence of an abnormality in a conveyance cart through immediate recognition of an incurred situation by a maintenance worker. This conveyance monitoring system is composed of a camera for taking a video of a running conveyance cart by following it automatically, a camera controller for controlling the camera, a video display device for displaying the video taken by the camera, a video recording device for recording the video taken by the camera, and other things. Monitoring the conveyance cart all the time with the camera, upon occurrence of an abnormality in the conveyance cart, the automatic conveying system automatically displays a video taken at the time of occurrence of the abnormality on the video display device. Furthermore, the automatic conveying system records a video taken from a start of conveyance to the occurrence of the abnormality and causes the video display device to reproduce and display it.

CITATION LIST

Patent Literature

Patent document 1: JP-A-2005-31900

SUMMARY OF INVENTION

However, in the above conventional conveyance monitoring system, observation targets located at such plural positions as not to be able to be shot directly, for example, located behind obstacles, by installing plural cameras for the respective observation targets. As a result, a large number of cameras need to be installed, resulting in increase in facility cost. Furthermore, the installation of a large number of cameras requires a large storage capacity for storage of videos taken, which is another factor in causing increase in facility cost.

The present invention has been made view of the above circumstances, and an object of the invention is therefore to provide a multi-positioning camera system capable of imaging, with at least one camera, observation targets located at such plural positions as no to be able to be shot directly and a camera system incorporating such multi-positioning cameras.

To attain the above object, the disclosure provides a multi-positioning camera system. The multi-positioning camera system includes an industrial endoscope in which an imaging device is provided in a tip portion of a flexible soft portion; a reel mechanism which pays out and takes up the soft portion by rotating, in a normal direction and a reverse direction, a reel drum around which a base portion of the soft portion is wound; a support pipe which supports the soft portion inserted from a tip of the support pipe in a pay-out direction; a distributor which places the tip portion of a portion, paid out from a support pipe opening formed at a destination-side tip of the support pipe, of the soft portion at one, selected by switching, of plural different positions; and plural branch pipes which have reception holes formed so as to correspond to the plural different positions, respectively, and observation windows that communicate with the reception holes and are located at the plural different positions, respectively, and each of which receives the soft portion inserted through the reception hole.

The disclosure also provides a camera system. The camera system includes plural multi-positioning camera systems each of which comprises an industrial endoscope in which an imaging device is provided in a tip portion of a flexible soft portion; a reel mechanism which pays out and takes up the soft portion by rotating, in a normal direction and a reverse direction, a reel drum around which a base-side portion of the soft portion is wound; a support pipe in which a portion, including the tip in a pay-out direction, of the soft portion is inserted; a distributor which places the tip portion of a portion, paid out from a support pipe opening formed at a destination-side tip of the support pipe, of the soft portion at one, selected by switching, of plural different positions; and plural branch pipes which have reception holes formed so as to correspond to the plural different positions, respectively, and observation windows that communicate with the respective reception holes and are located at the plural different positions, respectively, and each of which receives the soft portion inserted through the reception hole; and a camera control apparatus which stores one, selected by switching, of videos taken by the industrial endoscopes of the plural multi-positioning camera systems, respectively.

The multi-positioning camera system according to the disclosure makes it possible to image, with at least one camera, observation targets located at such plural positions as not to be able to be shot directly.

The camera system according to the disclosure makes it possible to efficiently image, with at least one camera, observation targets located at such plural positions as not to be able to be shot directly and to suppress increase of a video recording capacity.

DESCRIPTION OF EMBODIMENT

Specific configurations and operations of a multi-positioning camera system and a camera system according to an embodiment of the present disclosure will be hereinafter described in detail by referring to the accompanying drawings when necessary. However, unnecessarily detailed descriptions may be avoided. For example, detailed descriptions of well-known items and duplicated descriptions of constituent elements having substantially the same ones already described may be omitted. This is to prevent the following description from becoming unnecessarily redundant and thereby facilitate understanding of those skilled in the art. The following description and the accompanying drawings are provided to allow those skilled in the art to understand the disclosure thoroughly and are not intended to restrict the subject matter set forth in the claims.

Embodiment 1

Figure 1:
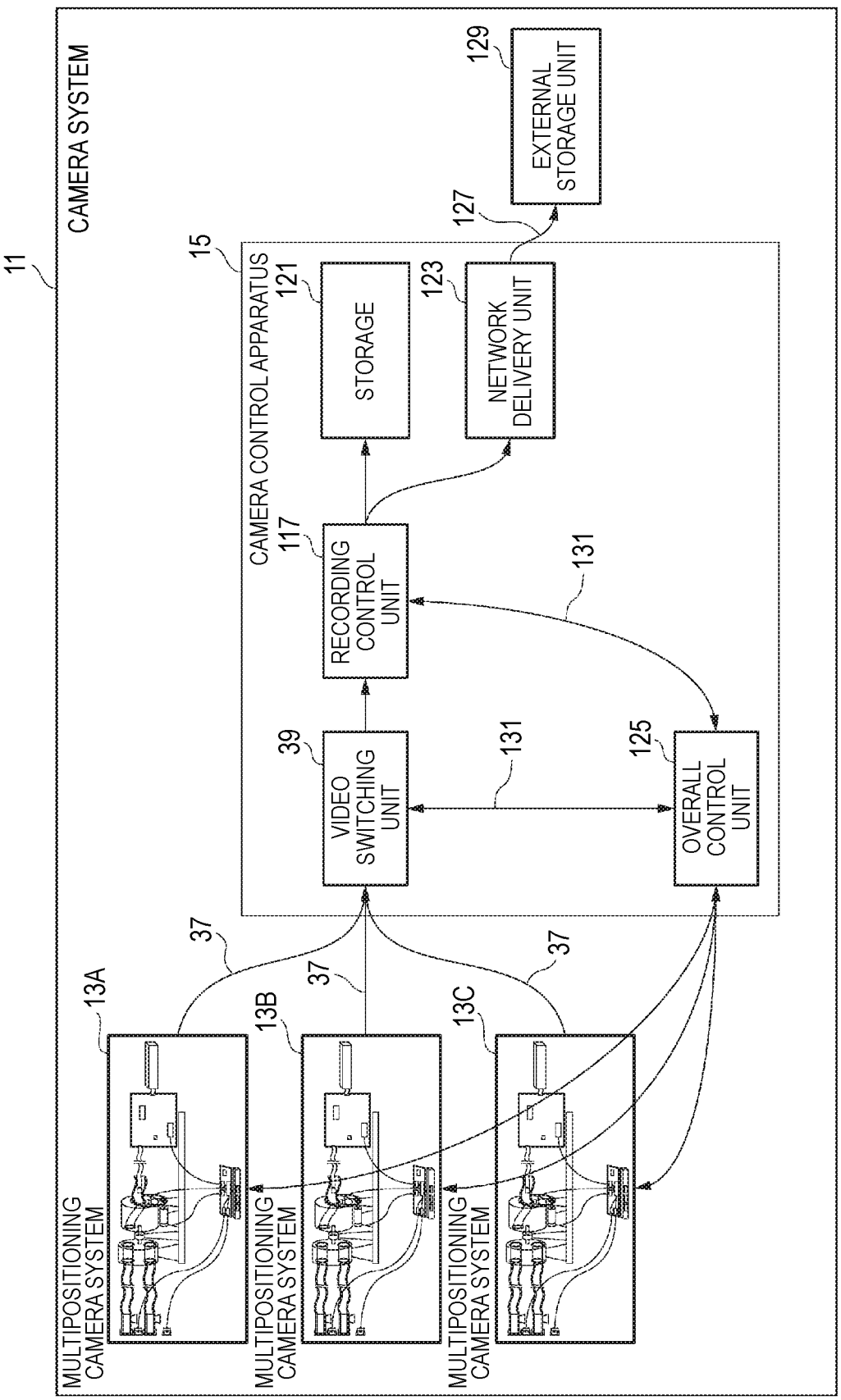
FIG. 1 is a block diagram showing an example internal configuration of a camera system according to an embodiment.

FIG. 1 is a block diagram showing an example internal configuration of a camera system 11 according to the embodiment.

The camera system 11 according to the embodiment is equipped with plural multi-positioning camera systems 13, a camera control apparatus 15, and an external storage unit 129. Installed in a clean room (not shown) of a semiconductor manufacturing factory, an electronic component factory, or the like, the camera system 11 observes whether a deterioration or failure has occurred in each of plural conveyance carts (e.g., unmanned conveyance carts) to run in the factory. The number of multi-positioning camera systems 13 (see FIG. 1) may be larger or smaller than three.

The camera system 11 is equipped with at least one multi-positioning camera system 13. Although the camera system 11 according to the embodiment is equipped with three multi-positioning camera systems 13, it goes without saying that the number of multi-positioning camera systems 13 is not limited to three.

Equipped with at least one endoscope camera 33, each of the plural multi-positioning camera systems 13A, 13B, and 13C is configured so as to be able to image plural imaging locations. The plural multi-positioning camera systems 13A, 13B, and 13C are connected to the camera control apparatus 15 by respective video output cables 37 and output videos taken by the endoscope cameras 33 to the camera control apparatus 15.

The camera control apparatus 15 performs switching between videos that are input from the plural multi-positioning camera systems 13A, 13B, and 13C, recording and output of the thus-selected video, and other operations according to a user manipulation. The camera control apparatus 15 is composed of an overall control unit 125, a video switching unit 39, a recording control unit 117, a storage 121, and a network delivery system 123.

The overall control unit 125 controls the operations of the individual units of the camera control apparatus 15. Functioning as a control unit of the camera control apparatus 15, the overall control unit 125 performs control processing for centralized control of the individual units of the camera control apparatus 15, data input/output processing with the individual units of the camera control apparatus 15, data computation (calculation) processing, and data storing processing. The overall control unit 125 operates by running programs that are stored in a ROM provided in a memory. The overall control unit 125 switches between videos taken by the endoscope cameras 33 that are input from the plural multi-positioning camera systems 13A, 13B, and 13C and stores the thus-selected video. The overall control unit 125 may control imaging positions P1, . . . , Pn of the endoscope cameras 33 of the plural multi-positioning camera systems 13A, 13B, and 13C according to a user manipulation.

The memory (not shown), which is provided in the overall control unit 125, includes, for example, a RAM (random access memory) and a ROM (read-only memory), is connected to the individual units of the camera control apparatus 15, and stores programs and data that are necessary for operation of the individual units and temporarily stores information, data, etc. generated during operations. The term "individual units" as used therein the overall control unit 125, the video switching unit 39, the recording control unit 117, the storage 121, and the network delivery system 123. For example, the RAM is a work memory that is used during operations of the individual units. For example, the ROM is stored in advance with the programs and data that are necessary for controlling the individual units.

The video switching unit 39 is connected to the plural multi-positioning camera systems 13A, 13B, and 13C by the plural video output cables 37, respectively. The video switching unit 39 switches between the endoscope cameras 33 (connection destinations) of the plural multi-positioning camera systems 13A, 13B, and 13C according to a control signal that is input from the overall control unit 125. The video switching unit 39 output a video taken by the selected endoscope camera 33 to the recording control unit 117.

The recording control unit 117 stores the video taken by the selected endoscope camera 33 to which connection is made by the video switching unit 39, on the basis of a control signal that is input from the overall control unit 125. The recording control unit 117 converts the received video of the endoscope camera 33 into a prescribed format by performing what is called encoding and outputs a resulting video to the storage 121 and the network delivery system 123.

The storage 121, which functions as a recorder, has a large storage capacity and is provided with video recording/reproduction software. The storage 121 stores and reproduces videos of the endoscope cameras 33 that are or have been input from the recording control unit 117.

The network delivery system 123 is connected to the external storage unit 129 by a bidirectional communication LAN cable 127 so as to be able to communicate with it. The network delivery system 123 outputs a video taken by an endoscope camera 33 and received from the recording control unit 117 to the external storage unit 129 via the bidirectional communication LAN cable 127.

The external storage unit 129 is connected to the network delivery system 123 by the bidirectional communication LAN cable 127 so as to be able to communicate with it. The external storage unit 129, which functions as a recorder, has a large storage capacity and is provided with video recording/reproduction software. The external storage unit 129 stores and reproduces videos of the endoscope cameras 33 that are or have been input from the recording control unit 117.

The external storage unit 129 may be integrated with an internal file system (not shown) inside the camera. For example, videos may be recorded in a removable medium such as a USB (Universal Serial Bus) memory or an SD (Secure Digital) card. In this case, although the external storage unit 129 is limited in storage capacity, only effective videos can be stored efficiently by controlling a recording start instruction and a recording stop instruction externally.

A remote monitoring system for the automatic conveyance carts causes the cameras installed at a manufacturing site to take videos indicating operation states of the automatic conveyance carts, sends the videos to a monitoring room, and monitors a video of a conveyance cart where trouble has occurred. The camera system 11 is used for imaging the automatic conveyance cart involved in the trouble. The installation site of the camera system 11 is not limited to a manufacturing line of an industrial product or the like.

Figure 2:
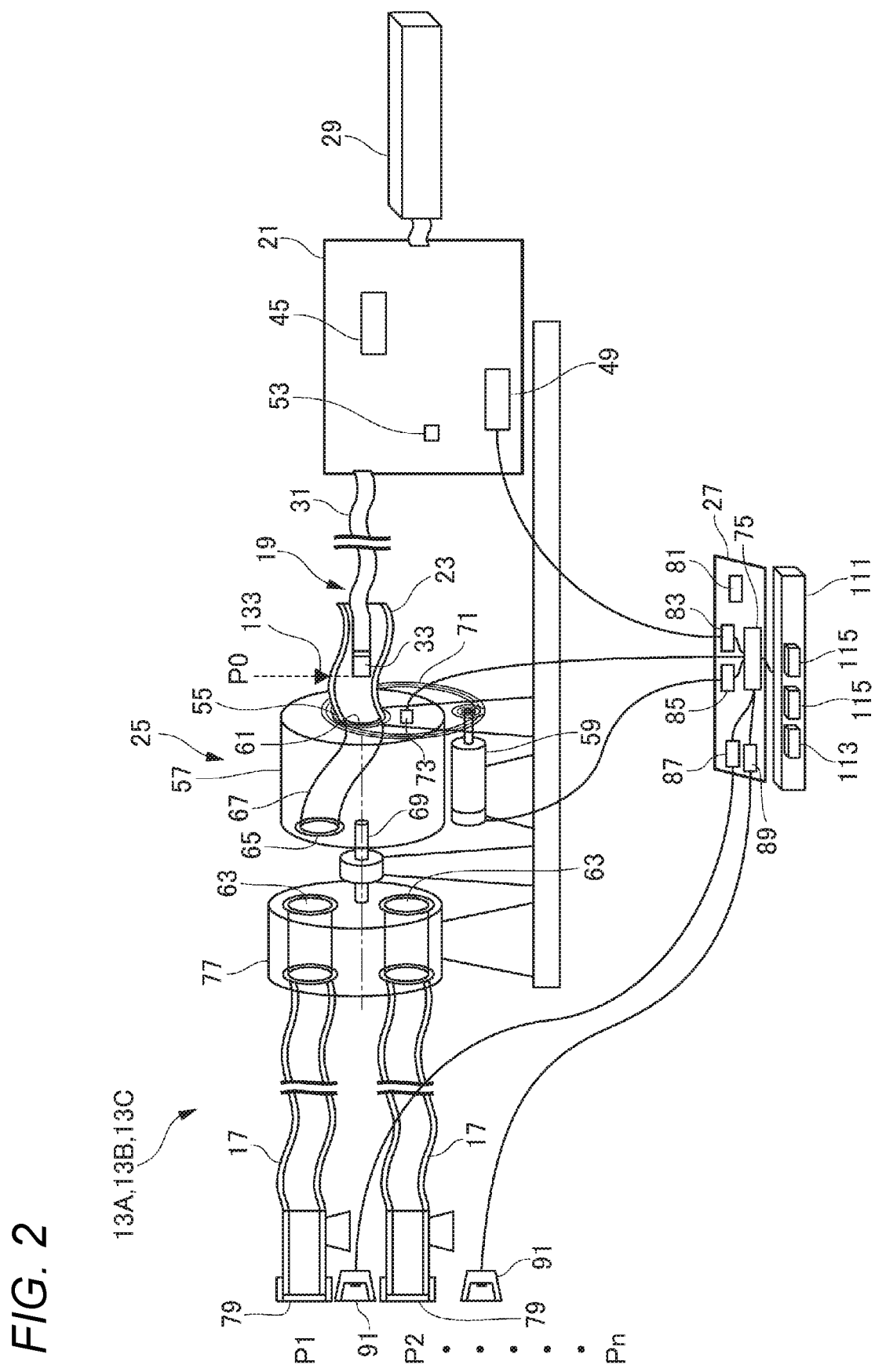
FIG. 2 is a schematic diagram showing an example internal configuration of each of plural multi-positioning camera systems.

Next, the configuration of each of the plural multi-positioning camera systems 13A, 13B, and 13C will be described with reference to FIG. 2. FIG. 2 is a schematic diagram showing an example internal configuration of each of the plural multi-positioning camera systems 13A, 13B, and 13C. FIG. 2 shows a state that an endoscope 19 is in a state that an endoscope camera 33 has been moved to a retraction position P0 in response to pushing of a retraction switch 113 of a switch unit 111. In this state, the endoscope camera 33 (i.e., a tip portion of the endoscope 19) is located at the retraction position P0 in a support pipe 23. The plural multi-positioning camera systems 13A, 13B, and 13C are the same except the positions and number of branch pipes 17 and reception holes 63 and the positions and number of illumination devices 91 and branch destination designation switches 115 that vary depending on the positions and number of branch pipes 17 and reception holes 63. Thus, the plural multi-positioning camera systems 13B and 13C will not be described below.

The multi-positioning camera system 13A is equipped with the endoscope 19, a reel mechanism 21, the support pipe 23, a distributor 25, branch pipes 17, a control unit 27, a camera control unit 29, and a pipe holder 77.

The endoscope 19 is configured so as to include a flexible soft portion 31 and the endoscope camera 33 attached to a tip portion of the soft portion 31. The endoscope 19 is an industrial endoscope and is about 1 to 10 mm in diameter.

The endoscope camera 33 is attached to a tip portion of the soft portion 31 and the soft portion 31 is provided with a plug (not shown) at the rear end (i.e., on the side of the reel mechanism 21). The plug electrically connects the endoscope camera 33 and the camera control unit (CCU) 29. The soft portion 31 has a covering that is a flexible member (e.g., resin tube). The soft portion 31 has such a length as to be able to move from the retraction position P0 to each of plural imaging positions P1, . . . , Pn (more specifically, positions of cylindrical tip caps 93 that are fixed to the respective branch pipes 17.

Power and various signals are transmitted from the camera control unit 29 to the endoscope 19 by transmission cables 43 (see FIG. 6) that are inserted in the soft portion 31. Image data taken by the endoscope camera 33 of the endoscope 19 is transmitted to the video switching unit 39 via the camera control unit 29.

In the endoscope 19, an elastic wire (not shown) attached to the endoscope camera 33 is inserted through the soft portion 31 to the plug. The elastic wire has a prescribed sectional area and is made of such a material as a metal having a wide elastic range. The elastic wire is flexible, is hard to deform plastically, and has a prescribed degree of flexural rigidity.

Since the elastic wire extends from the endoscope camera 33 to the plug, even if pay-out force is applied to the endoscope 19 from the plug side (base side), pushing force is transmitted to the endoscope camera 33 because of the prescribed flexural rigidity of the elastic wire. As a result, even if the outer diameter of the endoscope 19 is as small as, for example, 1 mm or less, the endoscope 19 is given so high pushability as to be able to reach an observation target position that is several meters ahead with a low probability of occurrence of buckling.

The reel mechanism 21, which is installed between the distributor 25 and the camera control unit 29, pays out and takes up the endoscope 19. The reel mechanism 21 pays out or takes up the soft portion 31 by rotating a reel drum 45 in the normal direction or the reverse direction by a reel motor 49. The reel mechanism 21 is configured so as to include the reel drum 45, the reel motor 49, and a reel sensor 53.

The reel drum 45 holds the endoscope 19 in such a manner that the soft portion 31 is wound around it. The reel drum 45 is driven rotationally by the reel motor 49.

The reel motor 49 receives, from a reel motor drive circuit 83, a control signal generated according to a user input manipulation performed on the switch unit 111. The reel motor 49 pays out or takes up the endoscope 19 according to the received control signal.

The reel sensor 53 measures a length of a portion, being paid out or taken up, of the endoscope 19 and outputs a measurement result or a measurement state to the control unit 27.

The support pipe 23 is a pipe for supporting a portion, being paid out or taken up by the reel mechanism 21, of the soft portion 31 at a position between the distributor 25 and the reel mechanism 21. When the retraction button 113 of the switch unit 111 is pushed by the user, the support pipe 23 supports the endoscope 19 in a state that its endoscope camera 33 is located at the retraction position P0. The support pipe 23 is shaped so as to have such an inner diameter as to be able to pay out or take up the soft portion 31 smoothly. Having a support pipe opening 55 at its distributor-25-side end, the support pipe 23 sends, to the distributor 25 through its switching inlet 61, a portion, being paid out by the reel mechanism 21, of the endoscope 19.

The distributor 25 or the support pipe 23 is provided with a P0 position detection sensor 133 which judges whether the tip portion of the endoscope 19, that is, the endoscope camera 33, is located at the retraction position P0. If detecting the endoscope camera 33, the P0 position detection sensor 133 judges that taking-up of the endoscope 19 has completed and outputs the judgment result to the reel mechanism 21. The reel mechanism 21 stops the taking-up of the endoscope 19 on the basis of the judgment result. The P0 position detection sensor 133 outputs the judgment result to the overall control unit 125.

The endoscope camera 33 which is located at the tip of a portion, paid out from the support pipe opening 55, of the soft portion 31 is inserted into the distributor 25. The distributor 25 performs positioning to send the endoscope 19 to the reception hole 63 that communicates with a user-selected one of the plural branch pipes 17.

The distributor 25 receives, from the control unit 27, a control signal generated according to a user manipulation performed on the switch unit 111 and rotates a rotary body 57 to a position corresponding to one, indicated by the control signal, of the reception holes 63. The distributor 25 is configured so as to include the rotary body 57, a rotary body motor 59, a bent tube 67, a rotary belt 71, and a rotation position sensor 73.

The pipe-holder-77-side end surface of the rotary body 57 is provided with a projection shaft 69 which serves as a rotation center shaft. The rotary body 57 is driven rotationally by the rotary body motor 59 via the rotary belt 71 and thereby rotated about the projection shaft 69. The rotary body 57 has, inside, the bent tube 67 through which the endoscope 19 is to pass.

The rotary body 57 is driven rotationally by the rotary body motor 59. The rotary body 57 is opposed to the support pipe opening 55 and has the switching inlet 61 (opening) which is coaxial with the rotation center axis. The rotary body 57 also has a switching outlet 65 which communicates with the switching inlet 61 and is to be opposed to the reception holes 63 of the plural branch pipes 17 when the rotary body 57 is rotated by different rotation angles, respectively. The switching inlet 61 and the switching outlet 65 are connected to each other by the bent tube 67 which penetrates through the rotary body 57.

The shape of the rotary body 57 is not limited to the one shown in FIG. 2. For example, the rotary body 57 may have such a thin cylindrical shape that its length along the axial line is shorter than its diameter. In this case, the rotation center axis of the rotary body 57 coincides with its axial line.

In such a thin rotary body 57, a switching inlet 61 (opening) is formed in one end surface, in the axial direction, of the rotary body 57 in such a manner that its axial line coincides with the rotation center axis. The switching inlet 61 may be formed as, for example, a tubular shaft that projects from the end surface of the rotary body 57. The tubular shaft has an insertion passage (bent tube 67) that is bent inside the rotary body 57, and a switching outlet 65 is opened in the other end surface of the rotary body 57 at a position that is opposite to the switching inlet 61 and is deviated from the rotation center axis by a prescribed distance. That is, a portion, inserted from the switching inlet 61, of the soft portion 31 is paid out toward the switching outlet 65 which is located at a position off the rotation center axis.

The projection shaft 69 or the like projects from the other end surface of the rotary body 57 so as to be coaxial with the rotation center axis. The rotary body 57 is supported rotatably in such a manner that a tubular shaft projecting from its one end surface and the projection shaft 69 projecting from its other end surface are supported rotatably. For example, the rotary body 57 is driven rotationally by a mechanism that a rotary belt 71 or a chain is stretched between the outer circumferential surface of the tubular shaft and a pulley of the rotary body motor 59.

The bent tube 67 is an insertion passage that is bent inside the rotary body 57, and has the switching inlet 61 and the switching outlet 65. The switching inlet 61 is, for example, a tubular shaft that is provided on the side of the support pipe 23 coaxially with the projection shaft 69 and projects from the support-pipe-23-side end surface of the rotary body 57 by a prescribed length. The switching outlet 65 is provided on the side of the pipe holder 77 so as to be deviated from the projection shaft 69 (i.e., from the rotation center axis of the rotary body 57) and to be opposed to each of the plural reception holes 63 of the pipe holder 77 when the rotary body 57 is rotated.

The rotary body motor 59 is pulse-controlled and driven rotationally so as to be rotated by a prescribed angle. A drive rotation angle of the rotary body motor 59 is detected by a rotation position sensor 73 and sent to a control microcomputer unit 75 of the control unit 27. The rotary body motor 59 receives, from the control unit 27, a control signal generated according to a user input manipulation performed on the switch unit 111 and is driven rotationally by a prescribed angle corresponding to the control signal. It is preferable to provide a speed reducer between the rotary body motor 59 and the pulley.

The rotation position sensor 73 is given a rotation angle for the rotary body motor 59 by the control microcomputer unit 75. If detecting that the rotary body motor 59 has rotated by the given rotation angle, the rotation position sensor 73 outputs a stop signal to the rotary body motor 59 and outputs a rotation angle of the rotary body motor 59 to the control microcomputer unit 75 of the control unit 27.

The camera control unit 29 is connected to the video switching unit 39 of the camera control apparatus 15 by the video output cable 37. The camera control unit 29 outputs a video taken by the endoscope camera 33 to the video switching unit 39.

The pipe holder 77 has the plural reception holes 63. The type of the pipe holder 77 is not limited to the revolver type shown in FIG. 2 and may be a slider type shown in FIG. 14. The revolver-type pipe holder 77 has the plural reception holes 63 that are arranged at prescribed intervals on a circle. On the other hand, the slider-type pipe holder 77 has plural reception holes 63 that are arranged at prescribed intervals on a straight line.

The plural reception holes 63 are formed at such positions as to correspond to the respective branch pipes 17. The rotary body 57 rotates the switching outlet 65 to a position corresponding to an imaging position selected by the user (i.e., a position of a reception hole 63 corresponding to a branch pipe 17 that leads to the imaging position). In this manner, the multi-positioning camera system 13A can form an insertion passage to the selected branch pipe 17.

The plural branch pipes 17 are associated with the reception holes 63 formed at the positions corresponding to plural different positions, respectively. The branch pipes 17 are fixed to the pipe holder 77 in an integrated manner at the positions corresponding to the reception holes 63, respectively. When the rotary body 57 of the distributor 25 is driven rotationally, the switching outlet 65 of the rotary body 57 is opposed to the reception hole 63 of one of the plural branch pipes 17 which are fixed to the pipe holder 77.

The plural branch pipes 17 have observation windows 79 that communicate with the reception holes 63, at their tips opposite to the reception holes 63, respectively. The plural branch pipes 17 are disposed at prescribed imaging positions where the user wants to image using the endoscope cameras 33, respectively. The plural branch pipes 17 correspond to the switches provided in the switch unit 111 to move the switching outlet 65 to the positions corresponding to the imaging positions P1, . . . , Pn, respectively. For example, the plural branch pipes 17 (i.e., plural observation windows 79) are disposed at respective positions in a pit where the automatic conveyance cart is to stand by. More specifically, for example, the plural observation windows 79 are disposed at such positions as to be able to image a bottom surface, individual wheels, movable portions, portions to wear, etc. of the automatic conveyance cart. The observation windows 79 of the respective branch pipes 17 are disposed so that their distances to the conveyance cart are equal to the focal length of the endoscope camera 33.

The plural branch pipes 17 are provided with illumination devices 91 for illuminating regions in front of the observation windows 79 (i.e., portions of the conveyance cart), respectively. The plural illumination devices 91, which are, for example, IR illumination devices or LEDs, illuminate locations to be shot by the endoscope camera 33. The plural illumination devices 91 are controlled by the control microcomputer unit 75. When receiving, from the reel mechanism 21, a detection signal indicating that the endoscope camera 33 has been located at one of the positions corresponding to the respective observation windows 79, the control microcomputer unit 75 turns on the corresponding one of the illumination devices 91 by driving the corresponding one of illumination drive circuits. Although only two illumination drive circuits, that is, a P1 illumination drive circuit 87 and a P2 illumination drive circuit 89, are provided in the example of FIG. 2, the invention is not limited to this case; the illumination drive circuits are provided in the same number as the branch pipes 17.

The control unit 27 controls the reel mechanism 21, the distributor 25, and the plural illumination devices 91 according to a user input manipulation performed on the switch unit 111. The control unit 27 is configured so as to include a power unit 81, the control microcomputer unit 75, the reel motor drive circuit 83, the rotary body motor drive circuit 85, and the plural illumination drive circuits.

The power unit 81 supplies power to the control unit 27.

The control microcomputer unit 75 generates a control signal for rotating the switching outlet 65 to a reception hole 63 that corresponds to a selected branch pipe 17 according to a user input manipulation performed on the switch unit 111. The control microcomputer unit 75 receives, from the reel mechanism 21, a detection result indicating that the endoscope camera 33 has reached the retraction position P0 and calculates a rotation angle formed by a current position of the switching outlet 65 and the position of a user-selected branch pipe 17 to be used next. The control microcomputer unit 75 outputs the calculated rotation angle to the rotation position sensor 73, the reel motor drive circuit 83, and the rotary body motor drive circuit 85. When receiving, from the reel mechanism 21, a detection signal indicating that the endoscope camera 33 has reached the tip portion of the selected branch pipe 17, the control microcomputer unit 75 controls the corresponding illumination drive circuit and thereby turns on the corresponding illumination device.

The reel motor drive circuit 83 generates a control signal on the basis of the rotation angle received from the control microcomputer unit 75 and outputs the generated control signal to the reel motor 49 of the reel mechanism 21.

The rotary body motor drive circuit 85 rotates the rotary body motor 59 by a prescribed rotation angle by pulse-controlling it.

The switch unit 111 is equipped with the retraction switch 113 for returning the endoscope camera 33 of the endoscope 19 to the retraction position P0 and plural branching destination designation switches 115 for moving the endoscope camera 33 to the imaging positions P1, . . . , Pn, respectively. The switch unit 111 functions as an interface for accepting a user manipulation. The switch unit 111 generates a control signal for controlling the control unit 27 according to a user input manipulation (i.e., an action of pushing a selected one of the plural switches) and outputs the generated control signal. The switch unit 111 judges whether taking-up of the endoscope 19 has been completed and outputs a judgment result to the reel mechanism 21.

Figure 3:
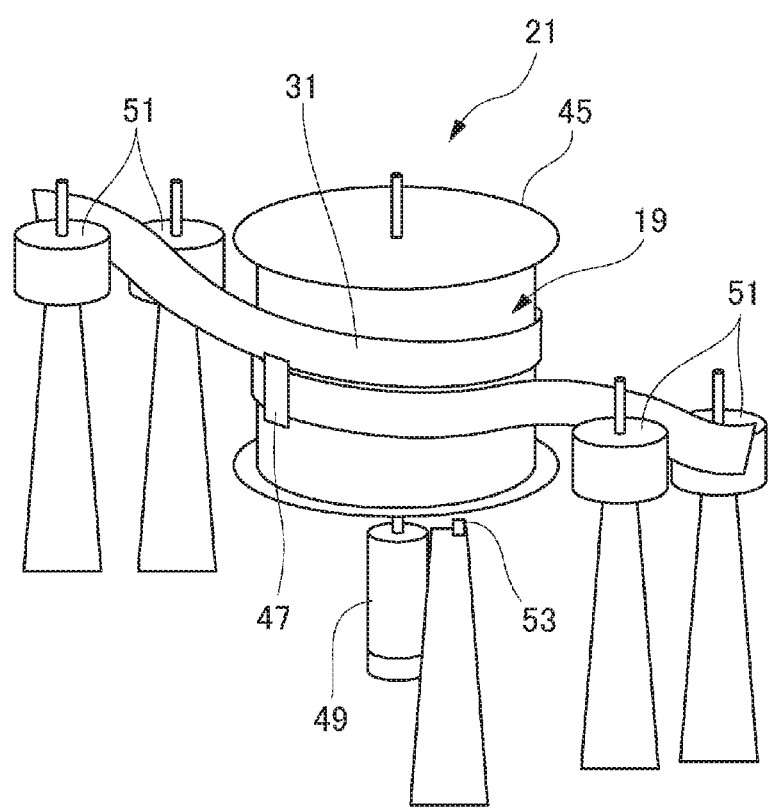
FIG. 3 shows an example configuration of a reel mechanism.

FIG. 3 shows an example configuration of the reel mechanism 21. The configuration of the reel mechanism 21 will be described with reference to FIG. 3.

In the reel mechanism 21, a base-side portion (camera-control-unit-29-side portion) of the soft portion 31, between the endoscope camera 33 and the plug (not shown), connected to the camera control unit 29, of the endoscope 19 is wound around the reel drum 45. A portion of the base-side portion of the soft portion 31 is fixed to the reel drum 45 by a fixing clamp 47. The reel mechanism 21 pays out or takes up the soft portion 31 by rotating the reel drum 45 in the normal direction or the reverse direction by the reel motor 49. The reel mechanism 21 may be equipped with a pair of or plural pairs of pinch rollers 51.

The pair of or plural pairs of pinch rollers 51 are rotated while pinching the soft portion 31 and thereby pay out or take up the soft portion 31. The reel drum 45 is equipped with the reel sensor 53 for detecting its rotation angle.

Figure 4:
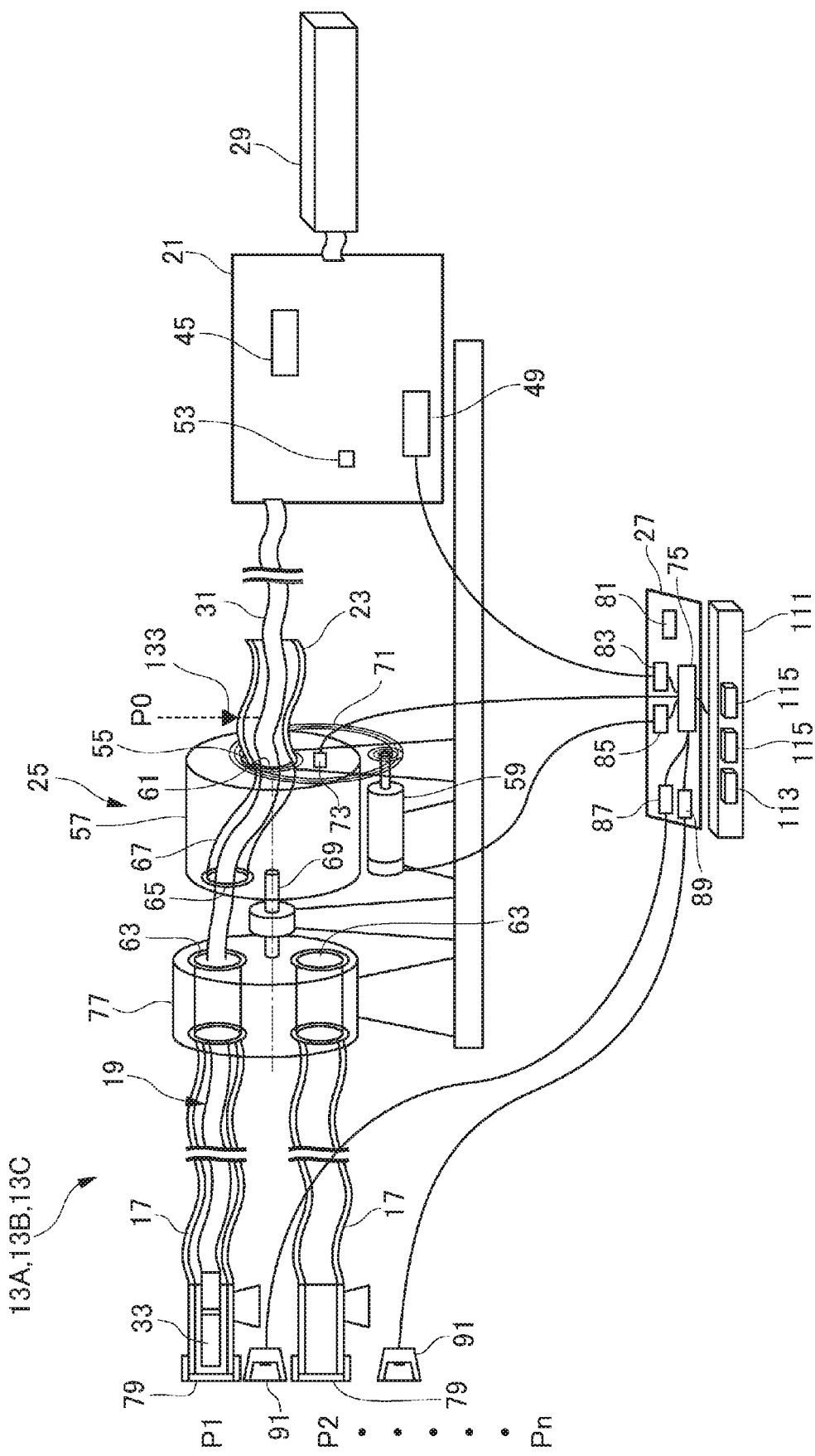
FIG. 4 is a schematic diagram showing an example internal configuration of a multi-positioning camera system in which an endoscope camera of an endoscope is located in a branch pipe (imaging position P1).

FIG. 4 is a schematic diagram showing an example internal configuration of the multi-positioning camera system 13A in which the endoscope camera 33 of the endoscope 19 is located in one branch pipe 17 (at the imaging position P). The endoscope camera 33 shown in FIG. 4 is inserted in the branch pipe 17 corresponding to the imaging position P1 among the plural branch pipes 17.

A portion of the soft portion 31 paid out from the reel mechanism 21 is inserted into the support pipe 23 from the side of the reel mechanism 21. The support pipe 23 has such an inner diameter as to allow the soft portion 31 to move through it smoothly. The support pipe 23 has the support pipe opening 55 on the side opposite to the pipe base end. A tip-side portion of the soft portion 31 is paid out from the support pipe opening 55.

The distributor 25 registers the switching outlet 65 with the reception hole 63 corresponding to the imaging position P1 among the plural imaging positions P1, . . . , Pn according to a user manipulation. The endoscope camera 33 is inserted through the distributor 25 from the support pipe opening 55 and the switching inlet 61 toward the switching outlet 65.

The reel mechanism 21 sends the endoscope camera 33 to the imaging position P1 selected according to a user manipulation. Upon completion of the sending of the endoscope camera 33 to the imaging position P1, the reel mechanism 21 outputs, to the control unit 27, a detection result to the effect that the sending has been completed. Upon receiving, from the reel mechanism 21, the detection result to the effect that the endoscope camera 33 has reached the observation window 79 located at the imaging position P1, the control unit 27 turns on the illumination device 91 located at the imaging position P1 by controlling the P1 illumination drive circuit 87.

When the illumination device 91 is turned on, the endoscope camera 33 which has been moved to the imaging position P1 starts imaging. Shooting by the endoscope camera 33 may be started at the same time as the turning-on of the illumination device 91. The overall control unit 125 receives a detection signal indicating that the endoscope camera 33 has been moved the imaging position P1 by the reel mechanism 21.

Figure 5:
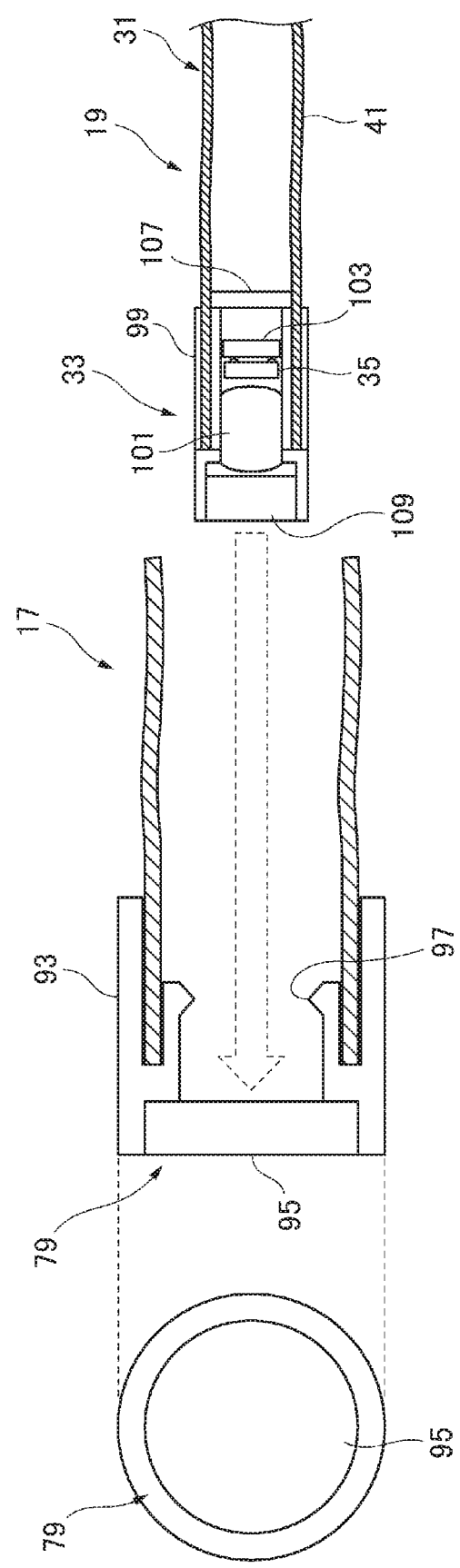
FIG. 5 is a front view and a side sectional view of an example branch pipe in a state immediately before insertion of the endoscope camera.

FIG. 5 is a front view and a side sectional view of an example branch pipe 17 in a state immediately before insertion of the endoscope camera 33.

Each of the plural observation windows 79 has a cylindrical tip cap 93 which is fixed to a tip portion of the branch pipe 17.

Each of the plural tip caps 93 has a cover glass 95 in its tip opening. A visible light cutting optical filter, a bandpass optical filter, an IR cutting optical filter, or the like is provided as the cover glass 95 as necessary. Each tip cap 93 is made of an elastic material such as rubber. Having plural camera holding projections 97 arranged in the circumferential direction, each tip cap 93 comes into contact with the inserted endoscope camera 33 elastically and holds the endoscope camera 33 coaxially with itself.

Figure 6:
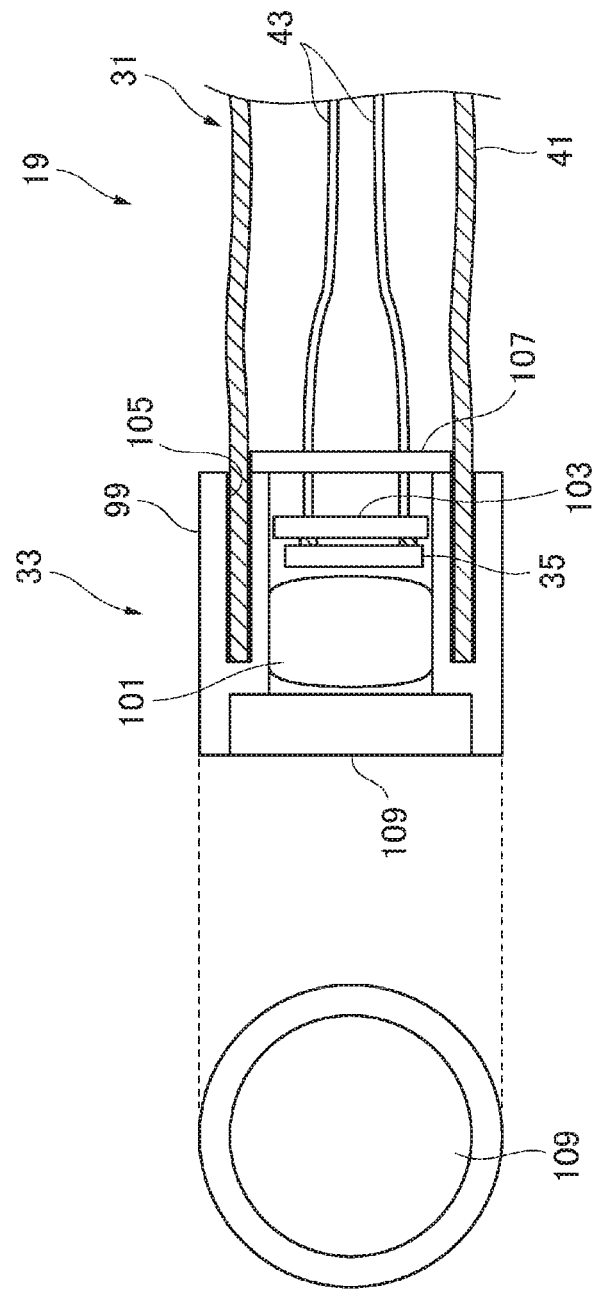
FIG. 6 is a front view and a side sectional view of an example endoscope camera of the endoscope.

FIG. 6 is a front view and a side sectional view of an example endoscope camera 33 of the endoscope 19.

The endoscope camera 33 of the endoscope 19 has an approximately cylindrical hard portion 99 made of stainless steel, for example. The hard portion 99 is configured so as to include, inside, an optical lens group 101, an imaging device 35, and a sensor connection circuit board 103. The rear end surface of the hard portion 99 is formed with a circumferential groove 105 which is concentric with the endoscope camera 33.

A tip portion of a resin tube 41 is inserted into and fixed to the circumferential groove 105. The rear opening of the hard portion 99 is closed by a partition wall 107 through which plural transmission cables 43 penetrate. The tip surface of the hard portion 99 is provided with an objective cover glass 109.

The optical lens group 101 is fixed to the inner circumferential surface of the hard portion 99 with adhesive. The optical lens group 101 consists of plural optical lenses. The term "adhesive" is not used here in such a strict sense as to mean a substance that is used for bonding surfaces of solid objects but used in such a broad sense as to mean a substance that can be used for connecting two objects or, in a case that solidified adhesive exhibits high barrier performance against a gas or a liquid, a substance that functions as a sealing material.

For example, the imaging device 35 is a small CCD (charge-coupled device) or CMOS (complementary metal-oxide-semiconductor) imaging device that is square when viewed from the front side or rear side. Incident light coming from the outside is focused on the imaging surface (not shown) of the imaging device 35 by the optical lens group 101. The imaging surface of the imaging device 35 is covered with a device cover glass.

The sensor connection circuit board 103 is disposed behind the imaging device 35 and is electrically connected to the plural transmission cables 43 which are a pair of power lines and a pair of signal lines.

Next, a description will be made of an example operation procedure of each of the plural multi-positioning camera systems 13A, 13B, and 13C.

Figure 7:
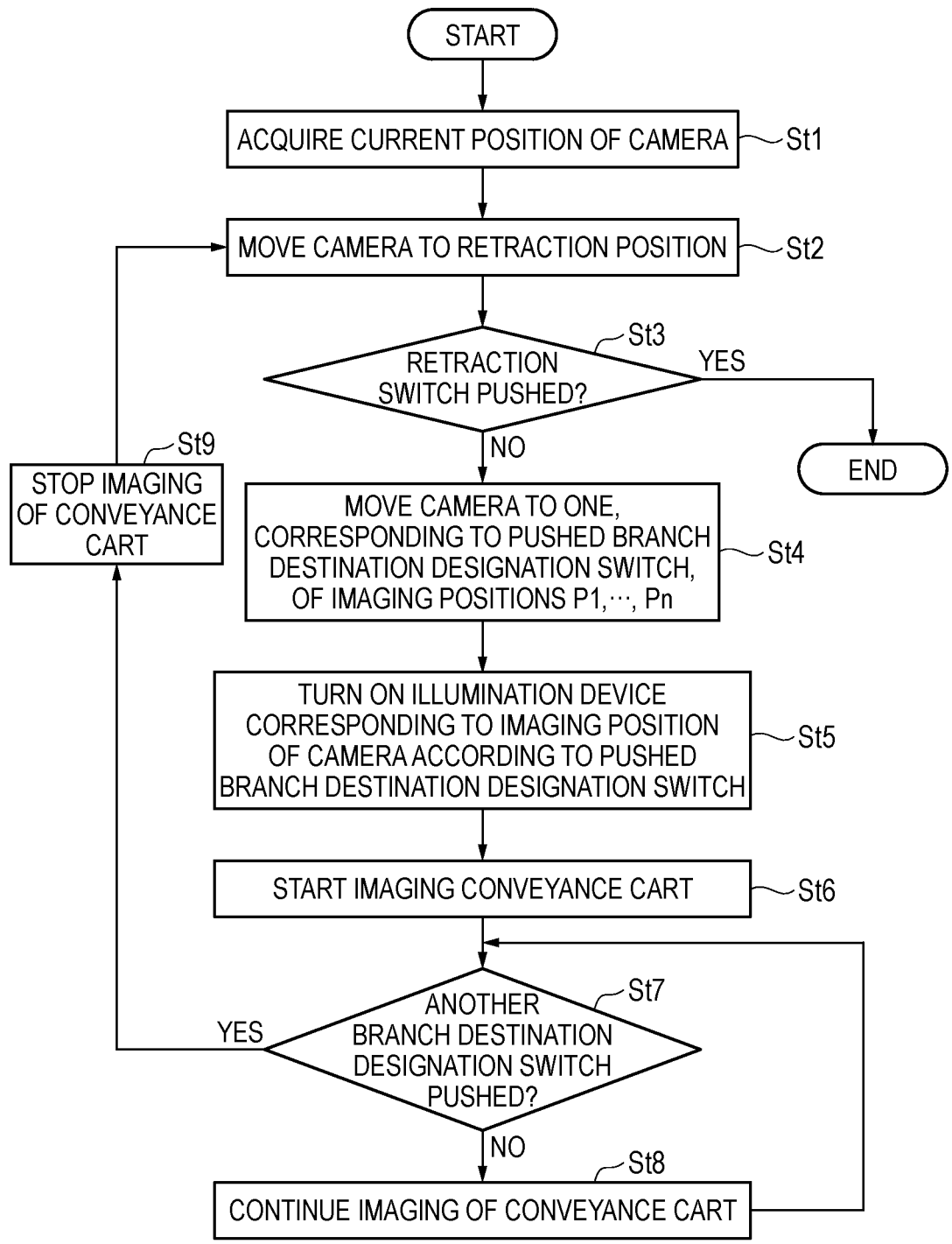
FIG. 7 is a flowchart showing the procedure of an example operation of imaging a conveyance cart with the endoscope camera from the positions, corresponding to plural imaging positions, of the branch pipes, respectively.

FIG. 7 is a flowchart showing the procedure of an example operation of imaging the conveyance cart with the endoscope camera 33 from the positions, corresponding to the imaging positions P1, . . . , Pn, of the branch pipes 17, respectively. In the following description, the term "retraction position P0" will be used as an initial position P0.

First, at step St1, the control unit 27 acquires a current position of the endoscope camera 33 of the endoscope 19.

At step St2, the control unit 27 moves the endoscope camera 33 to the retraction position P0. This prevents an event that the distributor 25 is rotated with the endoscope camera 33 located at one of the plural imaging positions P1, . . . , Pn and the endoscope 19 is thereby damaged. If the endoscope camera 33 is located at the retraction position P0, the control unit 27 causes the endoscope camera 33 to stay there.

At step St3, it is judged whether the retraction switch 113 was pushed by the user at step St2.

If it is judged at step St3 that the retraction switch 113 was pushed by the user (St3: yes), the process is rendered in a standby state.

On the other than, if it is judged that the retraction switch 113 was been pushed by the user and one of the plural branch destination designation switches 115 was pushed by the user (St: no), at step St4 the control unit 27 moves the endoscope camera 33 to the imaging position corresponding to the pushed branch destination designation switch 115.

At step St5, the control unit 27 controls the illumination drive circuit corresponding to the imaging position of the endoscope camera 33 according to the branch destination designation switch 115 pushed by the user and thereby turns on the corresponding illumination devices 91.

At step St6, the endoscope camera 33 starts imaging the conveyance cart from the prescribed imaging position corresponding to the branch destination designation switch 115 pushed by the user. A video taken by the endoscope camera 33 is output to the video switching unit 39 via the video output cable 37.

At step St7, all the time during which the endoscope camera 33 is imaging the conveyance cart from the prescribed imaging position, the control unit 27 judges whether another branch destination designation switch 115 has been pushed.

At step St8, the control unit 27 causes the endoscope camera 33 to continue the imaging of the conveyance cart unless another branch destination designation switch 115 was pushed by the user (St7: no).

If judging that another branch destination designation switch 115 was pushed by the user (St7: yes), the control unit 27 causes the endoscope camera 33 to stop imaging the conveyance cart.

After the execution of step St9, at step St2 the control unit 27 moves the endoscope camera 33 to the retraction position P0. Even if the user pushes the retraction switch 113 or one of the plural branch destination designation switches 115 during the execution of step St9, the control unit 27 moves the endoscope camera 33 to the retraction position P0.

If the user pushes one of the plural branch destination designation switches 115 during the execution of step St9, the control unit 27 may store information indicating the pushed branch destination designation switch 115 temporarily. In this case, the control unit 27 may execute the process as if the retraction switch 113 were not pushed at step St3 and execute step St4 onward according to the branch destination designation switch 115 pushed by the user.

The same procedure as described above is followed thereafter, whereby the conveyance cart is shot by the plural multi-positioning camera systems 13A, 13B, and 13C.

Figure 8:
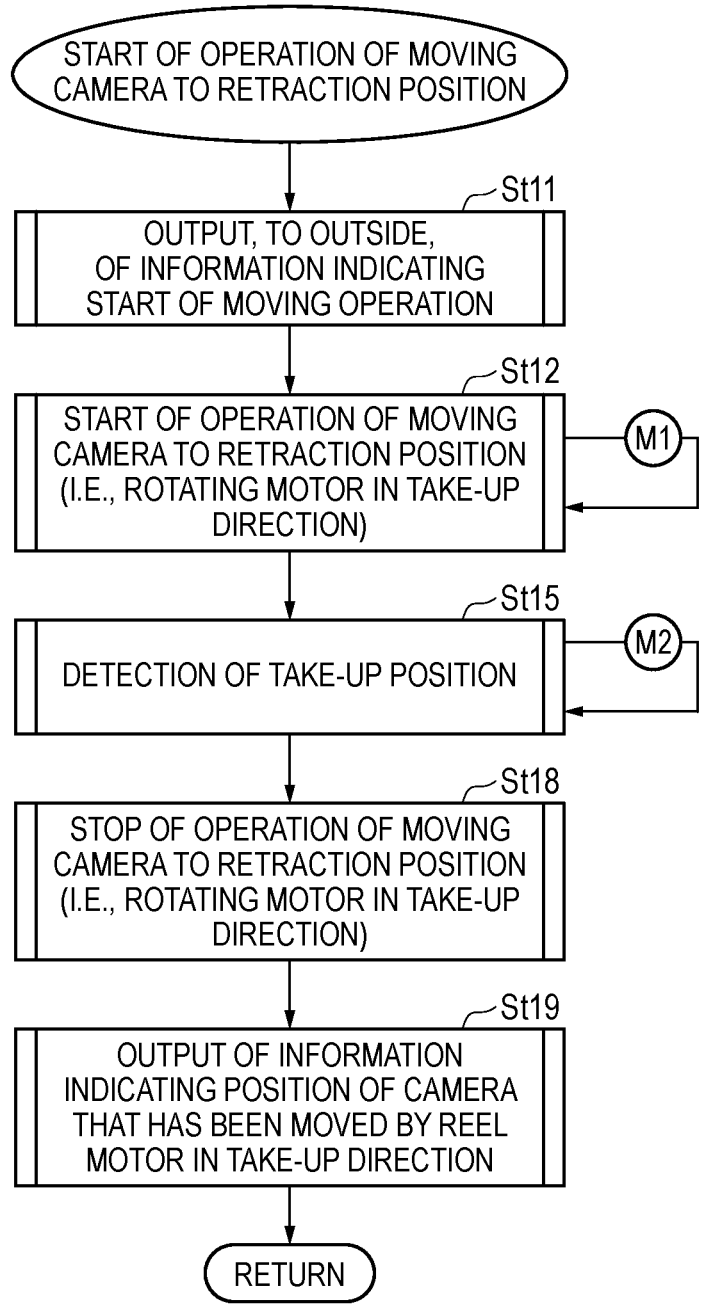
FIG. 8 is a flowchart showing an example procedure for moving the endoscope camera to a retraction position.
Figure 9:
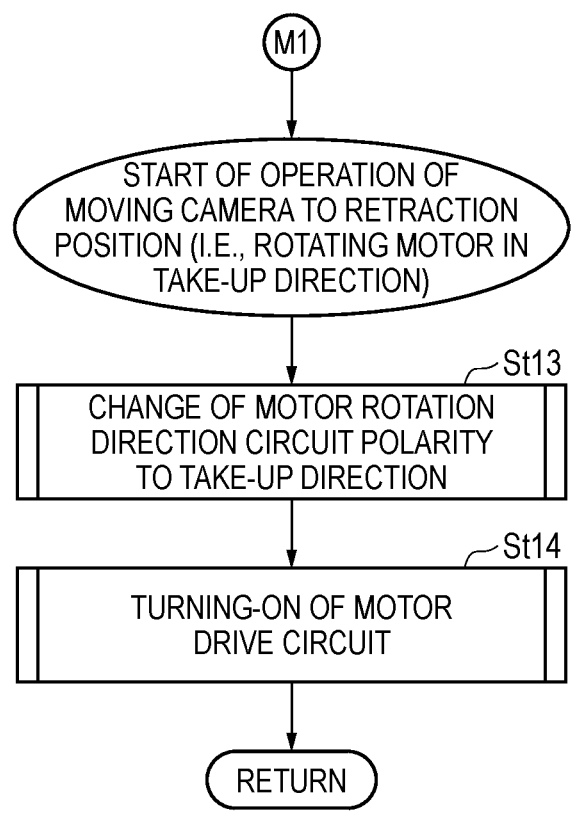
FIG. 9 is a flowchart showing an example procedure for controlling a reel motor to move the endoscope camera to the retraction position.
Figure 10:
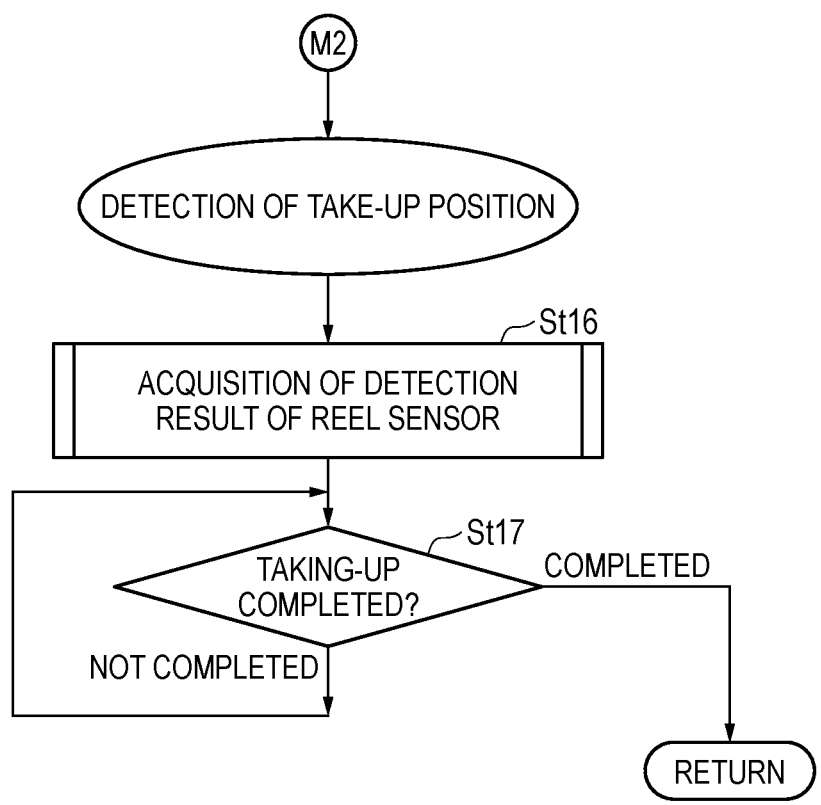
FIG. 10 is a flowchart showing an example taking-up control procedure that is followed by a reel mechanism.

Next, procedures for controlling the endoscope camera 33, the reel motor 49, and the reel mechanism 21 will be described in time-series order with reference to flowcharts of FIGS. 8-10. FIG. 8 is a flowchart showing an example procedure for moving the endoscope camera 33 to the retraction position P0. FIG. 9 is a flowchart showing an example procedure for controlling the reel motor 49 to move the endoscope camera 33 to the retraction position P0. FIG. 10 is a flowchart showing an example taking-up control procedure that is followed by the reel mechanism 21.

To move the tip portion (i.e., endoscope camera 33) of the camera to the retraction position P0, at step St11 the control unit 27 outputs, to the overall control unit 125 (i.e., to the outside), information indicating that an operation of moving the endoscope camera 33 to the retraction position P0 has been started. The procedure for controlling the reel motor 49 to move the endoscope camera 33 to the retraction position P0 will be described with reference to FIG. 9.

When an operation of moving the endoscope camera 33 to the retraction position P0 (i.e., rotating the reel motor 49 in the taking-up direction) is started at step St12, at step St13 the control unit 27 changes the rotation direction circuit polarity of the reel motor 49 to a take-up direction.

At step St14, the control unit 27 turns on the reel motor drive circuit 83 of the reel motor 49.

At step St12, the control unit 27 starts an operation of moving the endoscope camera 33 toward the retraction position P0 by driving the reel motor 49 in the take-up direction.

At step St15, the control unit 27 detects a current take-up position. A procedure for detecting completion of taking-up of the endoscope 19 will be described below with reference to the flowchart of FIG. 10.

The reel sensor 53, which is provided for the reel drum 45, measures a length of a paid-out or taken-up portion of the endoscope 19 and detects whether the retraction of the endoscope camera 33 has been completed on the basis of a measurement result. At step St16, the reel sensor 53 outputs a current measurement result to the control unit 27.

At step St17, the control unit 27 judges whether the retraction of the endoscope camera 33 has been completed on the basis of the measurement result received from the reel sensor 53.

If judging that the movement to the retraction position has been completed (St17: completed), at step St18 the control unit 27 stops the operation of moving the endoscope camera 33 to the retraction position (i.e., rotating the reel motor 49 in the taking-up direction).

On the other hand, if judging that the movement to the retraction position has not been completed yet (St17: not completed), the control unit 27 continues the operation of moving the endoscope camera 33 to the retraction position (i.e., rotating the reel motor 49 in the taking-up direction) and judges again at step St17 whether the movement to the retraction position has been completed.

At step S19, the control unit 27 outputs, to the overall control unit 125 (i.e., to the outside), information indicating a position of the endoscope camera 33 that has been moved by the reel motor 49 in the retraction direction.

Following the above-described procedures, the multi-positioning camera system 13 completes the movement of the endoscope camera 33 to the retraction position P0.

Figure 11:
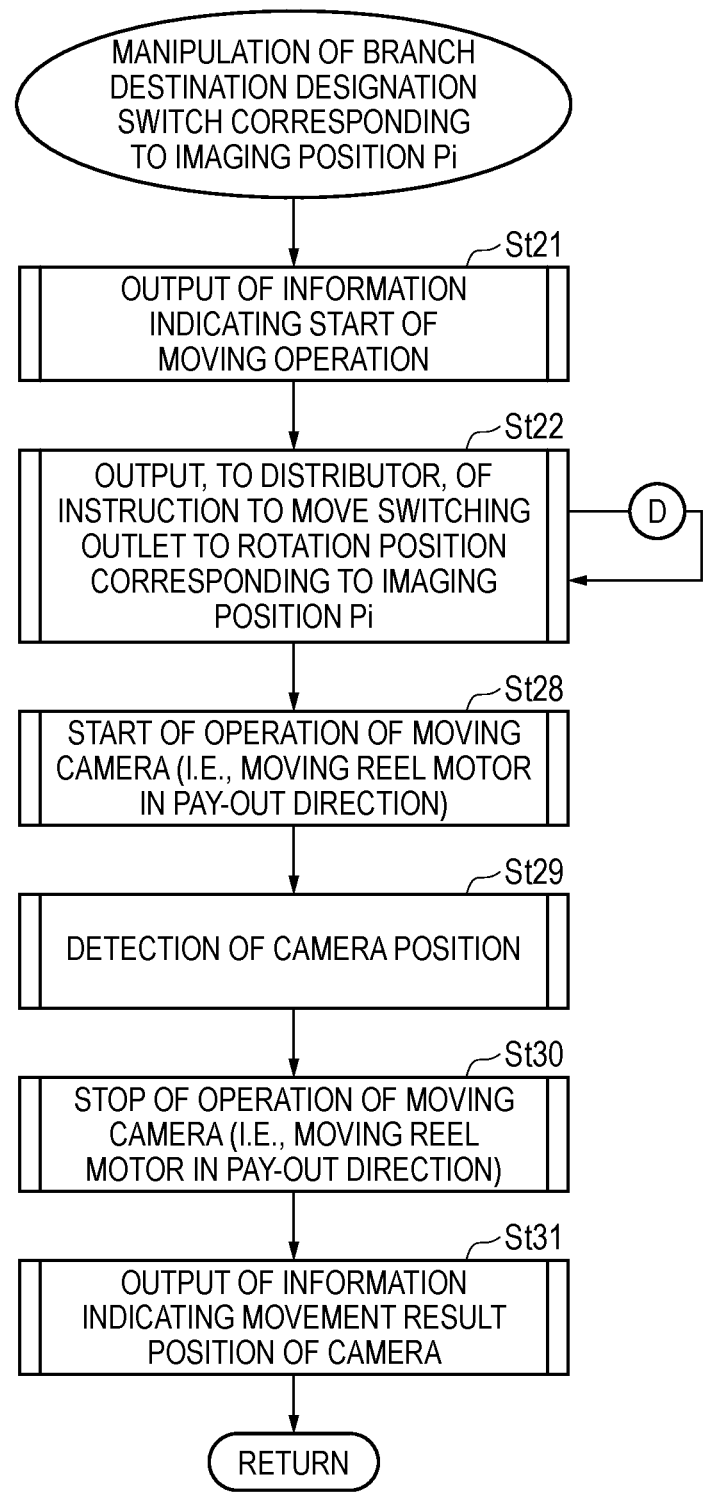
FIG. 11 is a flowchart showing an example control procedure to be followed in response to manipulation of a branch destination designation switch.
Figure 12:
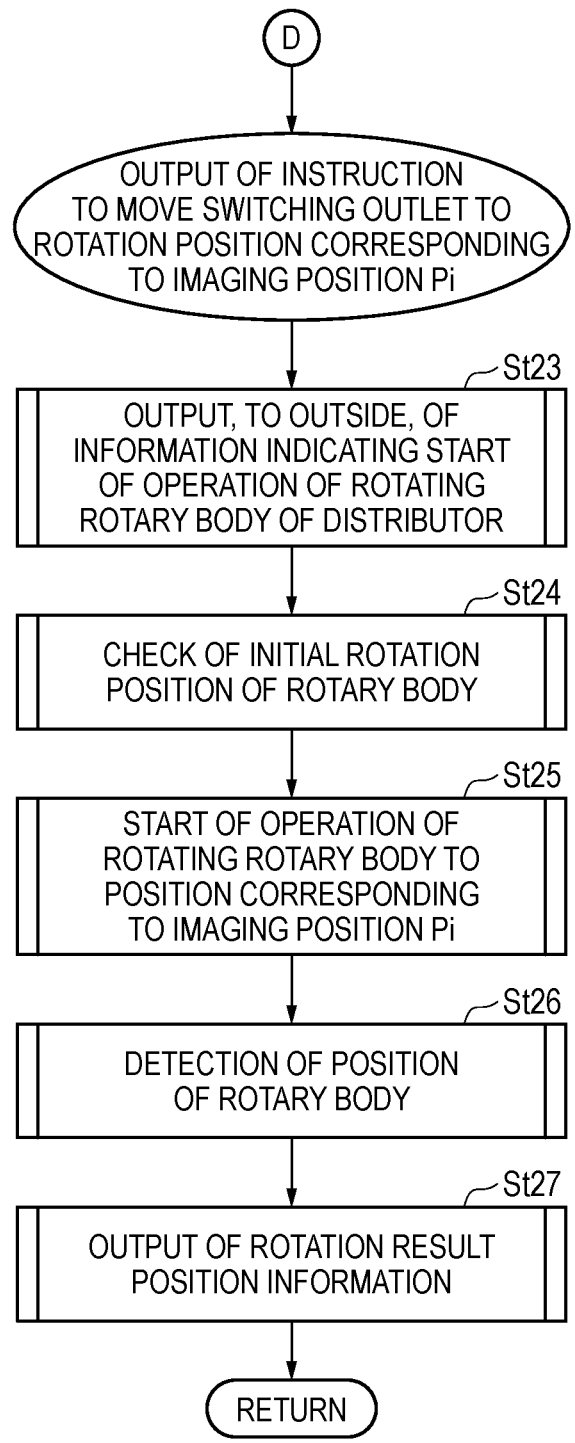
FIG. 12 is a flowchart showing an example procedure for controlling the distributor.

Next, a procedure for controlling movement of the endoscope camera 33 to one imaging position Pi among the imaging positions P1, . . . , Pn other than the retraction position will be described with reference to FIGS. 11 and 12. FIG. 11 is a flowchart showing an example control procedure to be followed in response to manipulation of a branch destination designation switch 115. FIG. 12 is a flowchart showing an example procedure for controlling the distributor 25.

To move the endoscope camera 33 to an imaging position Pi (i.e., a position other than the retraction position P0), first, at step St21, the control unit 27 informs the overall control unit 125 that an operation of moving of the endoscope camera 33 has been started.

At step St22, the control unit 27 outputs, to the distributor 25, a control instruction to move the switching outlet 65 to a rotation position corresponding to the imaging position Pi that corresponds to the branch destination designation switch 115 pushed by the user. A procedure for controlling the distributor 25 will be described below with reference to the flowchart of FIG. 12.

At step St23, the control unit 27 outputs information indicating a start of an operation of rotating the rotary body 57 of the distributor 25 to the overall control unit 125 (i.e., to the outside) on the basis of the control instruction that was output to the distributor 25.

At step St24, the rotary body motor 59 checks an initial rotation position of the rotary body 57 in response to the information indicating the start of the operation of rotating the rotary body 57 of the distributor 25.

At step St25, the rotary body motor 59 starts driving, that is, starts rotating the rotary body 57 to the position corresponding to the imaging position Pi.

At step St26, the rotation position sensor 73 detects a current position of the rotary body 57 and outputs it to the control unit 27. The rotary body motor 59 continues to rotate the rotary body 57 until the switching outlet 65 reaches the position of the reception hole 63 corresponding to the imaging position P1.

At step St27, the control unit 27 outputs rotation result position information to the overall control unit 125 (i.e., to the outside) upon completion of the rotation of the rotary body 57.

Upon completion of the rotation of the rotary body 57, at step St28 the control unit 27 starts an operation of moving the endoscope camera 33 (i.e., rotating the reel motor 59 in the pay-out direction).

At step St29, the control unit 27 detects that the endoscope camera 33 has reached the imaging position P1.

At step St30, the control unit 27 stops the operation that the reel motor 49 moves moving the endoscope camera 33 (i.e., rotating the reel motor 59 in the pay-out direction).

At step St31, the control unit 27 outputs information indicating a movement result position of the endoscope camera 33 to the overall control unit 125 (i.e., to the outside). According to the above-described procedures, each of the multi-positioning camera systems 13A, 13B, and 13C completes the movement of the endoscope camera 33 to the imaging position P1.

Figure 13:
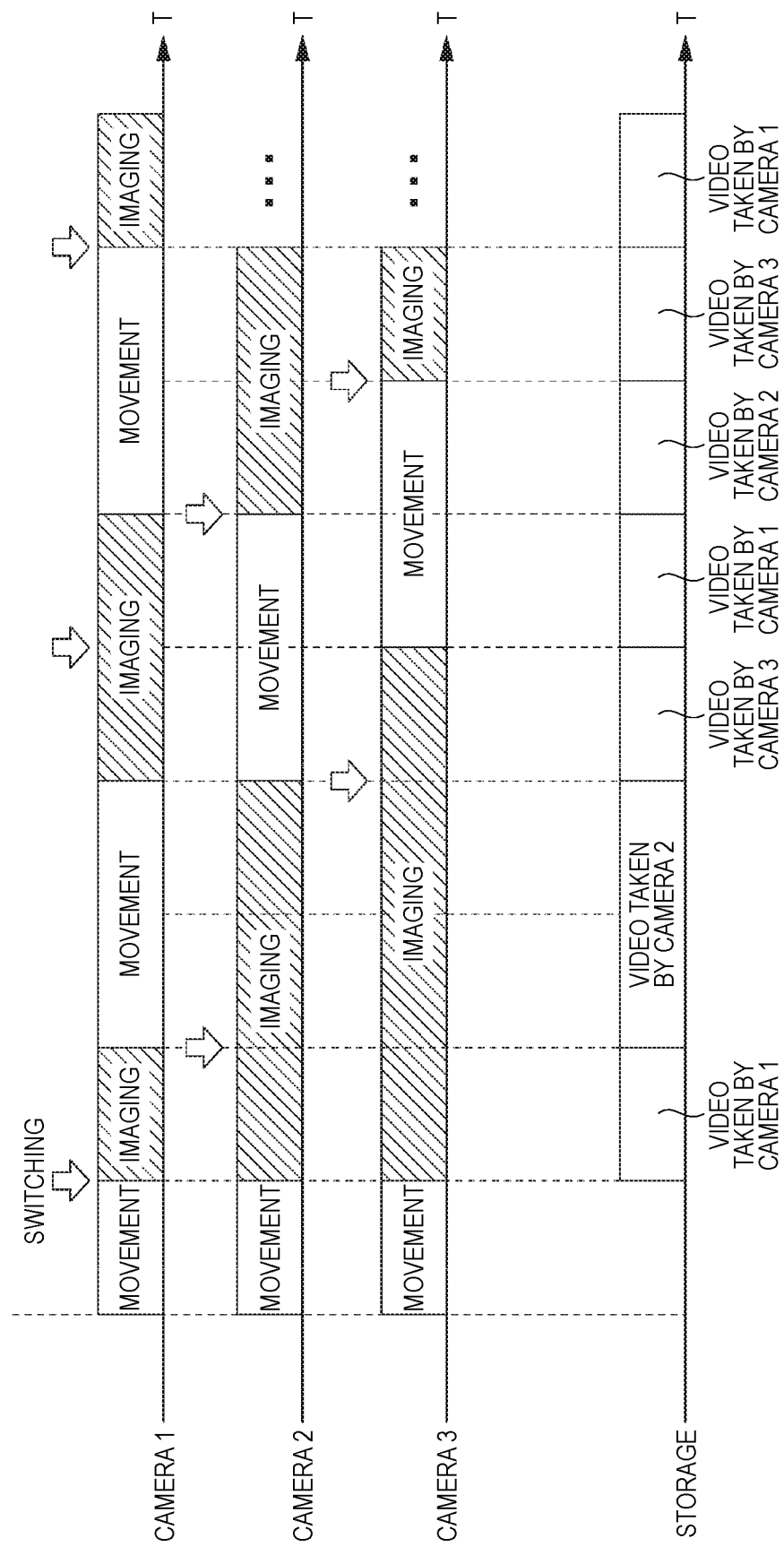
FIG. 13 is a timing chart showing a method for recording one video taken by each of the plural endoscope camera 33.

FIG. 13 is a timing chart showing a method for recording one video taken by each of the plural endoscope camera 33. The camera system 11 according to the embodiment is equipped with the plural multi-positioning camera systems 13A, 13B, and 13C. The camera control apparatus 15 records a video taken by the endoscope camera 33 of one of the multi-positioning camera systems 13A, 13B, and 13C.

The plural cameras 1, 2, and 3 shown in FIG. 13 are endoscope cameras 33 of the multi-positioning camera systems 13A, 13B, and 13C, respectively.

The term "storage" used in FIG. 13 is performed by a control of storing a video taken by one of the cameras 1, 2, and 3 according to a user manipulation.

The term "movement" used in FIG. 13 is performed in a time in which one of (or all of) the cameras 1, 2, and 3 is moved to one, selected by the user, of plural imaging positions P1, . . . , Pn. The cameras 1, 2, and 3 do not image while they are moving.

The term "switching" indicated by an arrow in FIG. 13 means a timing when the camera a video taken by which is to be stored is switched to another camera according to a user manipulation.

Referring to FIG. 13, first, the user performs a manipulation for storing a video taken by the camera 1 in a state that the cameras 1, 2, and 3 have started to move to the respective, prescribed imaging positions. Videos being taken by the respective cameras 1, 2, and 3 are displayed simultaneously in the video switching unit 39. The user switches to the camera that is imaging the video he or she wants to store and stores that video.

As described above, the camera system 11 according to the embodiment do not image unnecessary videos while the plural endoscope cameras 33 are being moved, that is, the endoscopes 19 are being paid out or taken up, and can select and store (record) only necessarily ones of videos being taken by the endoscope cameras 33 that have moved to prescribed imaging positions. As a result, in the camera system 11, the processing load can be reduced because useless imaging is not performed and a capacity-related load on the storage can be reduced because only videos that are necessary to the user are stored (recorded). Thus, videos taken can be stored efficiently.

Next, workings and advantages of the above-described multi-positioning camera system 13 according to the embodiment will be described below.

The multi-positioning camera system 13 according to the embodiment is equipped with the endoscope 19 in which the imaging device 35 is provided in the endoscope camera 33 of the flexible soft portion 31; the reel mechanism 21 which pays out and takes up the soft portion 31 by rotating, in the normal direction and the reverse direction, the reel drum 45 around which a base-side portion of the soft portion 31 is wound; the support pipe 23 in which a portion including the tip, in the pay-out direction, of the soft portion 31 is inserted; the distributor 25 which places the endoscope camera 33 of a portion, paid out from the support pipe opening 55 formed at the destination-side tip of the support pipe 23, of the soft portion 31 at one, selected by switching, of plural different positions; and the plural branch pipes 17 which have the reception holes 63 formed so as to correspond to the plural different positions, respectively, and the observation windows 79 that communicate with the reception holes 63 and are located at the plural different positions, respectively, and each of which receives the soft portion 31 inserted through the reception hole 63.

In the multi-positioning camera system 13 according to the embodiment, a base-side portion of the flexible soft portion 31 of the endoscope 19 is wound around the reel drum 45 of the reel mechanism 21. The reel mechanism 21 pays out and takes up the soft portion 31 by rotating the reel drum 45 in the normal direction and the reverse direction with the reel motor 49.

The endoscope camera 33 of a portion, paid out from the reel mechanism 21, of the soft portion 31 is inserted into the support pipe 23. The tip, in the insertion direction, of the support pipe 23 is the support pipe opening 55. The endoscope camera 33 of the portion, paid out from the reel mechanism 21, of the soft portion 31 is then inserted further through the support pipe opening 55.

The distributor 25 is opposed to the support pipe opening 55. The distributor 25 places the endoscope camera 33 of a portion, paid out from the support pipe opening 55, of the soft portion 31 at one of plural different positions (i.e., a user-selected one of the imaging positions P1, . . . , Pn). Since the soft portion 31 is flexible, the portion to the endoscope camera 33 paid out from the reel mechanism 21 of the soft portion 31 can be bent to any direction. Thus, the endoscope camera 33 of the soft portion 31 can be placed at one of the plural different positions by the distributor 25.

The reception holes 63 of the branch pipes 17 are formed so as to correspond to the plural different positions where the endoscope camera 33 is to be placed, respectively. That is, when the soft portion 31 is paid out further by the reel mechanism 21, the endoscope camera 33 to be placed at one, selected by switching, of the plural different positions is inserted through the corresponding reception hole 63. This reception hole 63 communicates with the observation window 79 formed at the tip of the corresponding one of the plural branch pipes 17. The observation window 79 of each branch pipe 17 can be placed at a desired position by bending the branch pipe 17. Thus, the endoscope camera 33 that has been inserted through the reception hole 63 of a desired branch pipe 17 reaches the observation window 79 by being paid out further by the reel mechanism 21. The conveyance cart can be shot from the observation window 79.

When the branch pipe 17 is bent in a desired direction, the soft portion 31 inserted therein is bent in the same direction. Thus, the endoscope camera 33 of the endoscope 19 can be placed at the position of a desired observation window 79 by taking up the soft portion 31 and then inserting it into another, desired branch pipe 17 using the distributor 25. In this manner, the multi-positioning camera system 13 can image, with at least one camera, observation targets that are located at plural positions and cannot be shot because, for example, they are located behind obstacles.

In the multi-positioning camera system 13, the illumination devices 91 are disposed adjacent to the tips of the plural branch pipes 17, respectively, to illuminate regions in front of the respective branch pipes 17 in their extension directions.

In this multi-positioning camera system 13, since the illumination devices 91 are disposed adjacent to the tips of the plural branch pipes 17, respectively, imaging by the imaging device 35 of the endoscope camera 33 which is located at the observation window 79 can be performing using the associated illumination device 91. The light emitted from each illumination device 91 may be visible light or infrared light. Since the illumination devices 91 are disposed adjacent to the tips of the plural branch pipes 17, respectively, the endoscope camera 33 need not be provided with an illumination window and hence the endoscope 19 can be reduced in diameter. Furthermore, since the illumination devices 91 are disposed adjacent to the tips of the plural branch pipes 17, respectively, the endoscope 19 can perform imaging with a sufficient light quantity that is not restricted by narrowing of the endoscope 19.

In the multi-positioning camera system 13, the distributor 25 has the rotary body 57 which is driven rotationally. The rotary body 57 is formed with the switching inlet 61 which is an opening opposed to the support pipe opening 55 and having the rotation center axis of the rotary body 57 as its axis and the switching outlet 65 which communicates with the switching inlet 61 and is opposed to the reception holes 63 of the plural branch pipes 17 when the rotary body 57 is rotated by different angles.

In this multi-positioning camera system 13, the distributor 25 has the rotary body 57. For example, the rotary body 57 may have such a thin cylindrical shape that its length along the axial line is shorter than its diameter.

The end surface, opposite to the end surface in which the switching inlet 61 is formed, of the rotary body 57 is formed with the switching outlet 65 (opening) at a position deviated from the rotation center axis. The switching outlet 65 is placed so as to be opposed to one of the reception holes 63, formed on a circle, of the plural branch pipes 17 by rotating the rotary body 57. Thus, the distributor 25 can send the endoscope camera 33 to the reception hole 63 of a desired branch pipe 17 from the switching outlet 65 by registering the switching outlet 65 with the reception hole 63 by rotating the rotary body 57 by a prescribed angle.

In the multi-positioning camera system 13, to insert, to another branch pipe 17, the endoscope camera 33 of the soft portion 31 that is inserted in one of the plural branch pipes 17, the endoscope camera 33 is returned from the branch pipe 17 to the distributor 25 or farther.

In the multi-positioning camera system 13, the passage from the reel mechanism 21 to the distributor 25 and each passage from the reception hole 63 of each branch pipe 17 to the corresponding observation window 79 are each an undividable insertion passage. On the other hand, the distributor 25 is moved relative to the branch pipes 17 to switch the branch pipe 17 into which the endoscope camera 33 is to be inserted. With this structure, in the multi-positioning camera system 13, a switching operation is realized that the soft portion 31 that is inserted in one branch pipe 17 is returned to the distributor 25 or farther beforehand to establish a state that the distributor 25 can be moved relative to the branch pipes 17 and then the endoscope camera 33 is inserted into another, desired branch pipe 17. As a result, in the multi-positioning camera system 13, an event can be prevented that the endoscope 19 is damaged because the distributor 25 is rotated with the endoscope camera 33 left at one of the imaging positions P1, . . . , Pn.

The multi-positioning camera system 13 is equipped with the one retraction switch 113 corresponding to the retraction position P0 to which the endoscope camera 33 is to be returned, the n branch destination designation switches 115 corresponding to the n respective branch pipes 17, and the control unit 27 which moves the endoscope camera 33 to a prescribed position by drive-controlling the reel mechanism 21 or the reel mechanism 21 and the distributor 25 according to a manipulation signal indicating which of the one retraction switch and the n branch destination designation switches 115 has been manipulated.

This multi-positioning camera system 13 is equipped with the retraction switch 113 for returning the endoscope camera 33 to the retraction position P0 and the n branch destination designation switches 115 for sending the endoscope camera 33 to a desired branch pipe 17. Each of the retraction switch 113 and the n branch destination designation switches 115 may be a manual push switch, for example.

Each of the retraction switch 113 and the n branch destination designation switches 115 is not limited to a push switch and may be a switching routine (program) for sending a drive control signal(s) to the reel mechanism 21 and/or the distributor 25 via an interface(s) in response to a manipulation signal sent from a host control device (e.g., overall control unit 125).

In the multi-positioning camera system 13, when the retraction switch 113 is manipulated, the reel mechanism 21 is driven, whereby the soft portion 31 is taken up so as to be wound around the reel drum 45. When detecting the endoscope camera 33, the P0 position detection sensor 133 judges that the taking-up of the soft portion 31 has been completed. When receiving, from the P0 position detection sensor 133, a judgment result to the effect that taking-up of the soft portion 31 has been completed, the reel mechanism 21 stops its operation. Position information indicating that the retraction of the endoscope camera 33 has been completed is output to an external device (e.g., overall control unit 125).

On the other hand, when one of the n branch destination designation switches 115 is manipulated, this manipulation is detected as information as an instruction to start an operation of moving the endoscope camera 33. That is, the control unit 27 confirms that the endoscope camera 33 is located at the retraction position P0. If the endoscope camera 33 is located at the retraction position P0, the control unit 27 outputs a movement instruction to the distributor 25. The distributor 25 rotates the rotary body 57 by an angle corresponding to the manipulated branch destination designation switch 115. When the switching outlet 65 has been moved so as to be opposed to the reception hole 63 of the branch pipe 17 corresponding to the manipulated branch destination designation switch 115, the distributor 25 or the control unit 27 outputs rotation result position information to the external device (e.g., overall control unit 125).

Then the reel mechanism 21 is driven and the endoscope camera 33 is sent from the retraction position P0 to the desired branch pipe 17 past the distributor 25. When the endoscope camera 33 reaches the observation window 79, a tip position of the endoscope camera 33 is detected, whereupon the sending operation of the reel mechanism is stopped. Thus, in the multi-positioning camera system 13, the switching of the branch pipe 17 in which a tip portion of the soft portion 31 is inserted to the branch pipe 17 designated by the branch destination designation switch 115 (i.e., designated by the user) is completed. Information indicating the position of the endoscope camera 33 after the switching of the branch pipe 17 is output to the external device (e.g., overall control unit 125).

The camera system 11 according to the embodiment is composed of the plural multi-positioning camera systems 13 each of which is equipped with the endoscope 19 in which the imaging device 35 is provided in the endoscope camera 33 of the flexible soft portion 31; the reel mechanism 21 which pays out and takes up the soft portion 31 by rotating, in the normal direction and the reverse direction, the reel drum 45 around which a base-side portion of the soft portion 31 is wound; the support pipe 23 in which a portion, including the tip in the pay-out direction, of the soft portion 31 is inserted; the distributor 25 which places the endoscope camera 33 of a portion, paid out from the support pipe opening 55 formed at the destination-side tip of the support pipe 23, of the soft portion 31 at one, selected by switching, of plural different positions; and the plural branch pipes 17 which have the reception holes 63 formed so as to correspond to the plural different positions, respectively, and the observation windows 79 that communicate with the respective reception holes 63 and are located at the plural different positions, respectively, and each of which receives the soft portion 31 inserted through the reception hole 63; and the camera control apparatus 15 which stores (records) one, selected by switching, of videos taken by the endoscopes 19 of the plural multi-positioning camera systems 13, respectively.

In the camera system 11 according to the embodiment, the camera control apparatus 15 selects and records a video taken by the endoscope camera 33 currently located at the observation window 79 among the plural endoscope cameras 33.

The camera system 11 performs operation controls so that a time to switch the branch pipe 17 in which a tip portion of the soft portion 31 is inserted to a desired branch pipe 17 (i.e., a time to move the endoscope camera 33) is used effectively for recording a video being taken by another endoscope 19. As a result, the camera system 11 can always record an effective video (efficient recording) and increase the image recording capacity by eliminating useless image information.

Figure 14:
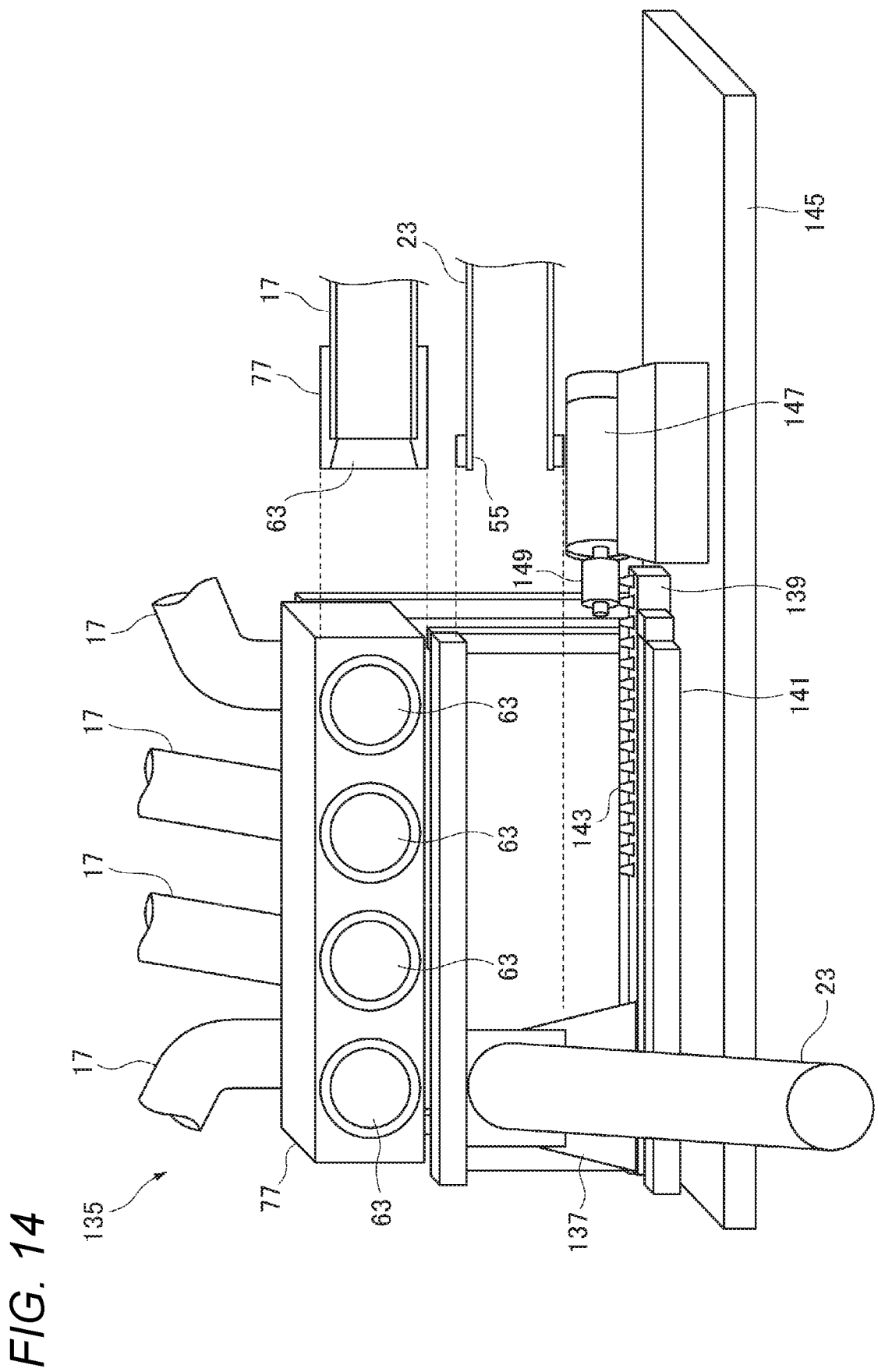
FIG. 14 shows an example slider-type distributor.

Next, the configuration of a slider-type distributor 135 which is a modified version of the above-described distributor 25 will be described. FIG. 14 shows an example slider-type distributor 135.

The slider-type distributor 135 of this modification has a slider 137 which is driven so as to reciprocate on a track. The slider 137 is fixed to a movable frame 139.

The movable frame 139 is put on a fixed rail 141 which constitutes the track. The movable frame 139 is formed with a rack 143. A sliding drive motor 147 is fixed to a stage 145 which is provided with the fixed rail 141. A pinion 149 which is fixed to the drive shaft of the sliding drive motor 147 is in mesh with the rack 143 of the movable frame 139. The sliding drive motor 147 is pulse-controlled and driven rotationally by a prescribed angle.

A support pipe 23, which is fixed to the slider 137, is formed in such a manner that at least a base-side portion having a prescribed length from a support pipe opening 55 is flexible. As a result, the support pipe opening 55 of the support pipe 23 can be moved to different positions with bending of a portion behind the support pipe opening 55 as the slider 137 is moved. When the slider 137 of the distributor 137 is moved to one of the different positions, the support pipe opening 55 is opposed to a corresponding one of reception holes 63 of plural respective branch pipes 17.

Next, workings and advantages of the slider-type distributor 135 of the modification will be described.

In the slider-type distributor 135 having the slider 137 which is driven so as to reciprocate, the flexible support pipe 23 is fixed to the slider 137 and the support pipe opening is opposed to one of the reception holes 63 of the plural branch pipes 17 when the slider 137 is moved to the corresponding one of the different positions.

In the distributor 135, the slider 137 reciprocates on the track. A portion, around the support pipe opening 55, of the support pipe 23 extending perpendicularly to the movement direction of the slider 137 is fixed to the slider 137. When the slider 137 is moved, the support pipe opening 55 of the support pipe 23 is opposed to one of the reception holes 63 of the plural branch pipes 17. In this manner, the distributor 135 can move the slider 137 to a desired slide position and thereby insert the endoscope camera 33 of a portion, paid out from the support pipe opening 55, of the soft portion 31 into the corresponding branch pipe 17 through its reception hole 63.

Conversely, the distributor 135 having the slider 137 may be configured in such a manner that the support pipe 23 is fixed in position and the slider 137 is provided with the plural branch pipes 17. In this case, each branch pipe 17 is formed in such a manner that at least its portion extending from the slider fixing portion and having a prescribed length is flexible. Also in the distributor 135 of this modification in which the branch pipes 17, rather than the support pipe 23, are located on the movable side, the endoscope camera 33 of a portion, paid out from the support pipe opening 55, of the soft portion 31 can be inserted into a desired branch pipe 17 through its reception hole 63 by registering the reception hole 63 of that branch pipe 17 with the support pipe opening 55 by moving the slider 137 to the corresponding slide position. The above-described multi-positioning camera system 13 according to the embodiment makes it possible to image, with at least one camera, observation targets located at plural positions that cannot be shot directly.

The above-described camera system 11 according to the embodiment makes it possible to efficiently image, with at least one camera, observation targets located at plural positions that cannot be shot directly and to suppress increase of the image recording capacity.

The camera system 11 may be installed in an automatic conveyance cart or a self-propelled inspection robot. In this case, videos of particular portions such as the bottom surface, wheels, and movable portions of the automatic conveyance cart or self-propelled inspection robot can be acquired by a small number of cameras installed. Since the number of cameras installed can be decreased, the self-propelled inspection robot or the like can be reduced in weight and size.

Although the camera system 11 according to the embodiment is directed to the case of imaging observation targets in a remote monitoring system for automatic conveyance carts, the invention is not limited to this case and can be applied to running vehicles (e.g., electric vehicles and railway vehicles) or facilities each having plural operating components to wear.

In the multi-positioning camera system 13, the retraction location of the industrial endoscope 19 and the branch pipes 17 may be given a radiation shielding structure. In the multi-positioning camera system 13, the industrial endoscope 19 etc. may be damaged if they are exposed to radiation for a long time in a work environment that is high in radiation dosage. Where the multi-positioning camera system 13 is installed in, for example, a self-propelled robot, it may be used in such a manner that the industrial endoscope 19 is usually retracted in a shielding structure and its tip portion is sent to the observation windows 79 when imaging needs to be performed. In this manner, damaging of the imaging device 35, the lens group 101, the board 103, the cables 43, etc. due to exposure to radiation can be suppressed.

Although the embodiment has been described above with reference to the accompanying drawings, it goes without saying that the disclosure is not limited to it. It is apparent that those skilled in the art would conceive various changes, modifications, replacements, additions, deletions, or equivalents within the confines of the claims, and they are construed as being included in the technical scope of the disclosure. Constituent elements of the above-described embodiment can be combined in a desired manner without departing from the spirit and scope of the invention.

INDUSTRIAL APPLICABILITY

The multi-positioning camera system and the camera system according to the disclosure are useful when used as a multi-positioning camera system and a camera system capable of imaging observation targets that are located at plural positions and cannot be shot directly.

What is claimed is:
1. A multi-positioning camera system comprising:
an industrial endoscope having an imaging device provided in a tip portion of a flexible soft portion;
a reel mechanism which pays out and takes up the soft portion by rotating, in a normal direction and a reverse direction, a reel drum around which a base portion of the soft portion is wound;
a support pipe which supports the soft portion inserted from a tip of the support pipe in a pay-out direction;
a distributor which has a rotationally-driven rotary body, and which switches and places a tip portion of the soft portion paid out from a support pipe opening formed at an insertion tip of the support pipe at one of a plurality of different positions; and a plurality of branch pipes which have reception holes arranged corresponding to the plurality of different positions and observation windows that communicate with the reception holes and are located at the plurality of different positions, and each of which receives the soft portion inserted through the reception hole, wherein the rotary body is formed with a switching inlet which is an opening opposed to the support pipe opening and having a rotation center axis of the rotary body as its axis and a switching outlet which communicates with the switching inlet and is opposed to the reception holes of the plurality of branch pipes when the rotary body is rotated by different angles.

2. The multi-positioning camera system according to claim 1, further comprising illumination devices which are disposed adjacent to tips of the plurality of branch pipes, respectively, and illuminate regions in front of the respective branch pipes.

3. The multi-positioning camera system according to claim 1, wherein the distributor has a slider which is reciprocated;

the support pipe is flexible and is fixed to the slider; and the support pipe opening is opposed to the reception holes of the plurality of branch pipes when the slider is moved to different positions.

4. The multi-positioning camera system according to claim 1, wherein in a case that the branch pipe into which the tip portion is inserted among the plurality of branch pipes is switched to another branch pipe, the tip portion of the soft portion is returned from one branch pipe to the distributor.

5. The multi-positioning camera system according to claim 4, further comprising one retraction switch corresponding to a retraction position to which the tip portion of the soft portion is to be returned;

a branch destination designation switch corresponding to each of the plurality of branch pipes; and a control unit which arranges the tip portion of the soft portion to a prescribed position by drive-controlling the reel mechanism or the reel mechanism and the distributor according to a manipulation signal indicating which of the one retraction switch and the branch destination designation switches has been manipulated.

6. A camera system comprising:

a plurality of multi-positioning camera systems including:
   an industrial endoscope having an imaging device provided in a tip portion of a flexible soft portion;
   a reel mechanism which pays out and takes up the soft portion by rotating, in a normal direction and a reverse direction, a reel drum around which a base-side portion of the soft portion is wound;
   a support pipe which supports the soft portion inserted from a tip of the support pipe in a pay-out direction;
   a distributor which has a rotationally-driven rotary body, and which switches and places a tip portion of the soft portion paid out from a support pipe opening formed at an insertion tip of the support pipe at one of a plurality of different positions; and
   a plurality of branch pipes which have reception holes arranged corresponding to the plurality of different positions and observation windows that communicate with the reception holes and are located at the plurality of different positions, and each of which receives the soft portion inserted through the reception hole; and a camera control apparatus which stores one, selected by switching, of image taken by the industrial endoscopes of the plurality multi-positioning camera systems, respectively, wherein the rotary body is formed with a switching inlet which is an opening opposed to the support pipe opening and having a rotation center axis of the rotary body as its axis and a switching outlet which communicates with the switching inlet and is opposed to the reception holes of the plurality of branch pipes when the rotary body is rotated by different angles.

* * * * *